(12) United States Patent  
Cheetham

(10) Patent No.: US 9,370,403 B2  
(45) Date of Patent: Jun. 21, 2016

(54) DENTAL CAPSULE

(71) Applicant: Joshua James Cheetham, Windsor (AU)

(72) Inventor: Joshua James Cheetham, Windsor (AU)

(73) Assignee: SDI North America Inc., Bensenville, IL (US)

( * ) Notice: Subject to any disclaimer, the term of this patent is extended or adjusted under 35 U.S.C. 154(b) by 0 days.

(21) Appl. No.: 14/247,315

(22) Filed: Apr. 8, 2014

(65) Prior Publication Data

US 2014/0305816 A1   Oct. 16, 2014

(30) Foreign Application Priority Data

Apr. 12, 2013 (AU) ................................. 2013901275

(51) Int. Cl.
*A61C 5/06* (2006.01)
*B65D 25/08* (2006.01)
(52) U.S. Cl.
CPC ................ *A61C 5/066* (2013.01); *A61C 5/068* (2013.01); *B65D 25/08* (2013.01)
(58) Field of Classification Search
CPC ........ A61C 17/00; A61C 5/066; A61C 5/064; A61C 5/068; B65D 25/08
See application file for complete search history.

(56) References Cited

U.S. PATENT DOCUMENTS

| | | | | |
|---|---|---|---|---|
| 3,415,360 A * | 12/1968 | Baumann | ............... | A61C 5/066 206/222 |
| 4,182,447 A * | 1/1980 | Kay | ....................... | A61C 5/066 206/220 |
| 5,088,830 A * | 2/1992 | Muhlbauer | ............ | A61C 5/064 366/108 |
| 5,509,530 A * | 4/1996 | Wilson | .................... | A61C 5/066 206/220 |
| 6,360,886 B1 * | 3/2002 | Welsh | .................... | A61C 5/066 206/219 |
| 6,439,380 B1 * | 8/2002 | Welsh | .................... | A61C 5/066 206/219 |

* cited by examiner

*Primary Examiner* — Andrew Perreault  
(74) *Attorney, Agent, or Firm* — William H. Holt

(57) ABSTRACT

A dental capsule (10) for storing a dental powder component (13) and a liquid component (28) in separated condition in which the powder component (13) is contained in a chamber (17) and the liquid component (28) is contained in a pouch (18). The capsule (10) comprises a freely movable member (36) arranged to rupture the pouch (18) upon vibration of the capsule (10) so that the liquid component (28) admixes with the powder component (13) to form a dental paste (38). The compartment of the capsule has a manually removable cap (14) to enable the dental paste (38) to be retrieved for use.

4 Claims, 3 Drawing Sheets

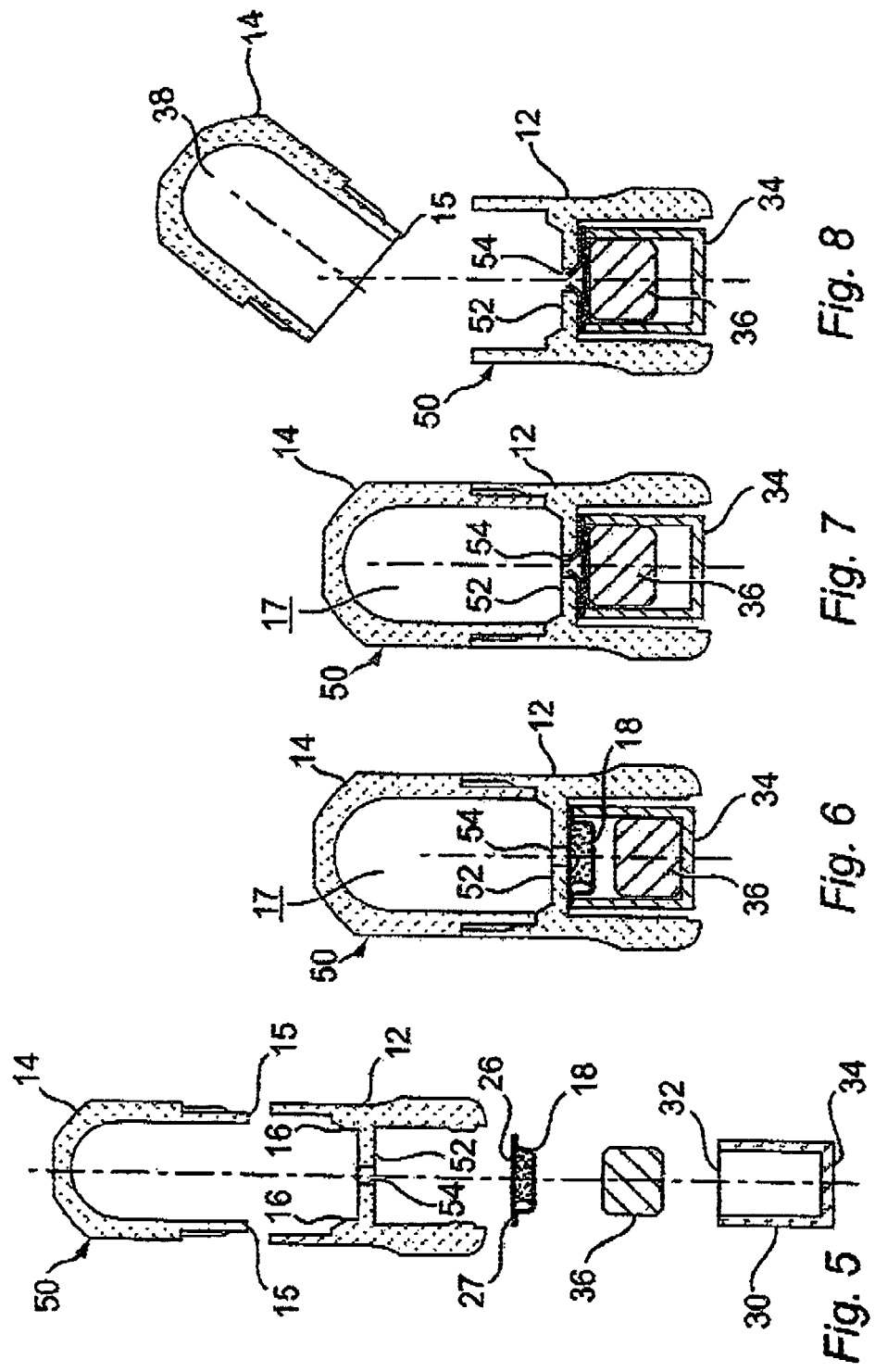

DENTAL CAPSULE

TECHNICAL FIELD

The present invention relates to a dental capsule

BACKGROUND

It is known to provide dental capsules containing dental powder and liquid in separated condition. The powder and liquid components are typically admixed by any convenient means and the capsule is subsequently placed in a mixing device. In the mixing device the components are thoroughly admixed to form a dental paste suitable for application to a tooth for treatment thereof.

It has now been discovered that it is possible to admix the components of a dental capsule simultaneously with vibration thereof.

SUMMARY OF THE INVENTION

In accordance with one aspect of the present invention there is provided a dental capsule comprising means for storing dental powder and liquid components in separated condition having a hollow body with a first end and second end, wherein the powder component is contained in a compartment of the hollow body adjacent the first end of the capsule and the liquid component is contained in a pouch adjacent the second end of the hollow body, the second end of the hollow body being provided with a chamber having an open outer end and a partially closed inner end, the chamber having mounted therein the pouch, a restraining cup being mounted in the open end of the chamber, the restraining cup having a closed outer end and an open inner end, the pouch being retained in place by engagement between the inner end of the cup and the inner end of the chamber, the cup further containing an unrestrained member disposed between an outer end of the cup and the pouch, the unrestrained member being arranged to move reciprocally within the cup when the capsule is vibrated in a vibrating mixer so as to impact against the pouch so as to rupture the pouch at the partially closed inner end of the chamber to enable the liquid component to admix with the powder component to form a dental paste simultaneously with vibration wherein the compartment of the hollow body adjacent the first end thereof is provided with a manually removable cup.

BRIEF DESCRIPTION OF THE DRAWINGS

The present invention will now be described, by way of example, with reference to the accompanying drawings, in which:

FIG. 5 is a transverse sectional view similar to FIG. 1 of a further embodiment of the capsule in accordance with the present invention;

FIG. 6 is a transverse sectional view of the capsule of FIG. 5 in assembled condition;

FIG. 7 is a view similar to FIG. 6 with the capsule in activated condition; and FIG. 8 is a view of the capsule of FIG. 5 in a separated condition after mixing has taken place.

DESCRIPTION OF THE PREFERRED EMBODIMENTS

Figure 1:
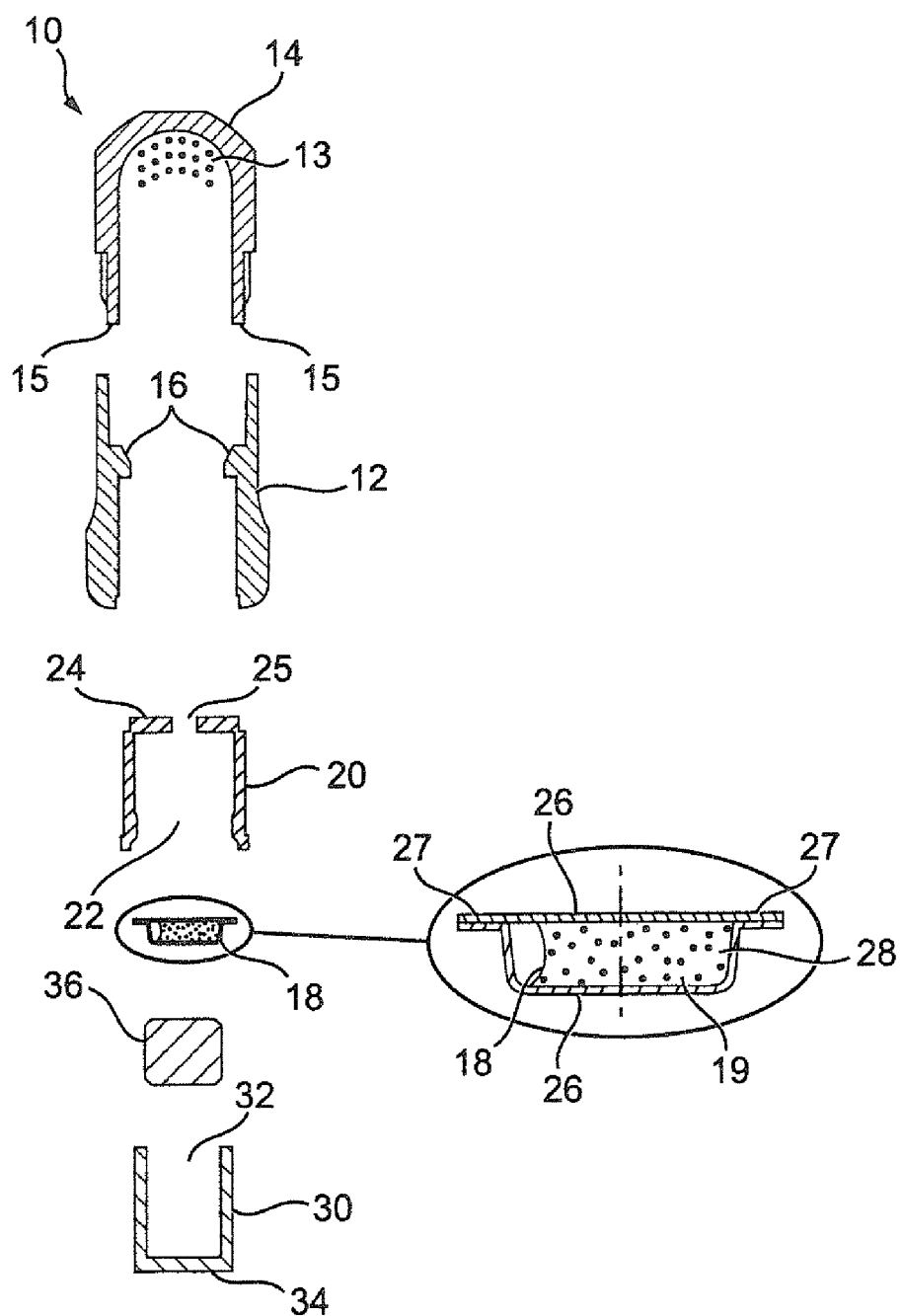
FIG. 1 is a transverse sectional view of a capsule in accordance with the present invention in exploded condition.
Figure 2:
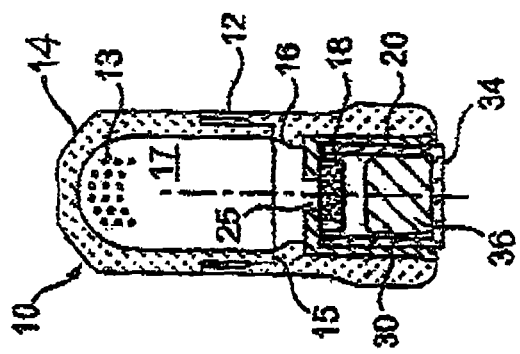
FIG. 2 is a transverse sectional view of the capsule of FIG. 1 in assembled condition.

In FIGS. 1 and 2 of the accompanying drawings there is shown a dental capsule 10, having a main body 12 and a removable cap 14, arranged to engage with an end of the body 12.

Figure 3:
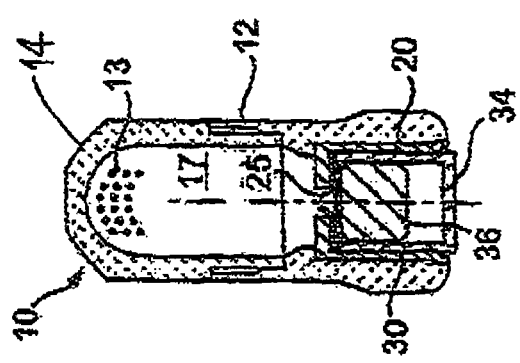
FIG. 3 is a view similar to FIG. 2 with the capsule in activated condition.

The body 12 has an internal circumferential flange 16. The cap 14 has an inner end 15 which engages with one side of the flange 16 as shown in FIG. 2. The cap 14 and the adjacent end of the body 12 form part of a chamber 17 containing a dental powder component 13, in use as seen in FIGS. 2 and 3.

Further, a liquid containing pouch 18 is mounted within a chamber 20. The chamber 20 has an outer open end 22 and a partially closed inner end 24 as shown in FIG. 2 containing a relatively small aperture 25. The chamber 20 engages with a side of the flange 16 opposite that engaged by the cap 14. The pouch 18 is mounted in the chamber 20 as will be described.

As shown in FIG. 1, the pouch 18 comprises a pair of opposed layers 26 which are typically formed of film. As shown one layer 26 is flat and the other is recessed so that the pouch 18 defines a volume 19 containing a liquid component 28. However, the volume 19 could be defined by the other layer 26 being recessed or by both layers 26 being recessed. The volume 19 is sized so as to hold an amount of liquid component compatible with the amount of the powder component in the chamber 17.

Edges 27 of the layers 26 forming the pouch 18 may be ultrasonically welded or laser welded or heat sealed together. Thus, the edges 27 of the layers 26 are then joined together to form a hermetic seal around the liquid containing volume 19.

The layers 26 may be made from mono, di or tri layered film. Film with more than three layers can be used. The flat layer 26 may be made thinner or weaker than the recessed layer 26.

The pouch 18 is retained in place initially by a restraining cup 30 which has an open inner end 32 and a closed outer end 34 as shown in FIGS. 1 and 2. As shown the cup 30 engages with the chamber 20. The inner end 32 of the cup 30 together with the inner end 24 of the chamber 20 sandwiches the edges 27 of the layers 26 in the assembled condition of the capsule 10 as can been seen in FIG. 2.

As shown, the chamber 17 is defined by the cap 14, the flange 16 and the inner end of the chamber 20.

Further, the cup 30 contains a freely mounted or unrestrained member 36 which is disposed in the volume between the outer end 34 of the cup 30 and the pouch 18. The member 36 may be a solid member which fits snugly in the cup 30. The member 36 may be made of plastics material. The member 36 is smaller longitudinally than the volume defined by the cup 30 and the pouch 18 and is therefore able to move reciprocally within the cup 30 when the capsule 10 is placed in a vibratory mixer.

In use, the capsule 10 in assembled condition is inserted in a vibratory dental mixer of known type. As the capsule 10 is vibrated the unrestrained member 36 is moved reciprocally in the volume between the outer end 34 of the cup 30 and the pouch 18. Thus, the unrestrained member 36 impacts the adjacent layer 26 of the pouch 18 repeatedly. This causes the adjacent layer 26 to be depressed. Further this action causes hydraulic pressure of the liquid component 28 in the pouch 18 to be increased so that the layer 26 of the pouch 18 adjacent the aperture 25 in the inner end of the chamber 20 is ruptured at the aperture 25 as shown in FIG. 3. This creates a path for the liquid component 28 to contact powder in the cap 14 for mixing in the chamber 17. Generally, a mixing time of 5 to 15 seconds such as about 10 seconds is sufficient for the liquid component 28 in the pouch 18 to be forced into the chamber 17.

Figure 4:
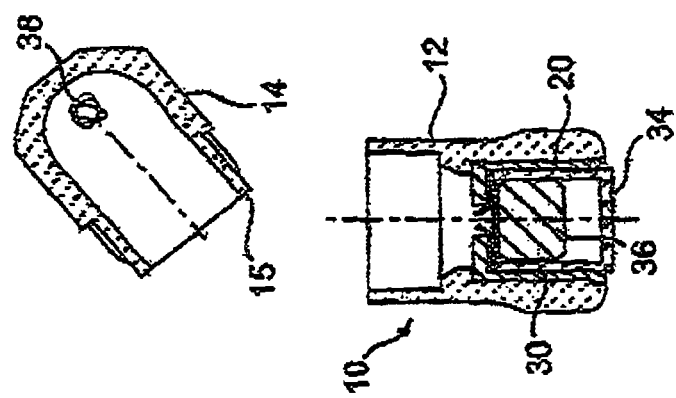
FIG. 4 is a view of the capsule of FIG. 2 in a separated condition after mixing has taken place.

After mixing the cap 14 may be removed manually as shown in FIG. 4 so that mixed dental paste 38 can be accessed.

The capsule 50 of FIGS. 5 to 8 is an embodiment which is similar to that of FIGS. 1 to 4 and like reference numerals denote like parts.

In the capsule 50 the flange 16 supports a partition 52 containing a central aperture 54. The partition 52 forms an inner end of the chamber 17 and is integrally formed with the flange 16. Further, a layer 26 of the pouch 18 is disposed adjacent the aperture 54.

In this embodiment the pouch 18 is retained in place initially by a retaining cup 30 which has an open inner end 32 and a closed outer end 34. The inner end 32 of the cup 30 engages with the partition 52 as shown in FIG. 6 and sandwiches the edges 27 of the layers 26. In this embodiment the chamber 17 is defined by the cap 14, the flange 16 and the partition 52.

In this embodiment, construction of the capsule is very similar to that of the embodiment of FIGS. 1 to 4. In this case a layer 26 of the pouch 18 adjacent the aperture 52 is ruptured as shown in FIG. 7.

The mixed dental paste 38 in this activated capsule can be retrieved in similar manner to that of FIGS. 1 to 4 by manually removing the cap 14 as shown in FIG. 8.

Modifications and variations as would be apparent to a skilled addressee are deemed to be within the scope of the present invention.

The invention claimed is:

1. A dental capsule comprising a dental powder component and a liquid component in separated condition, said dental capsule having a hollow body with a first end and a second end, wherein said powder component is contained in a compartment of said hollow body adjacent said first end of said hollow body and said liquid component is contained in a pouch adjacent said second end of said hollow body, said second end of said hollow body being provided with a receptacle having an open outer end and a partially closed inner end, said pouch being mounted in said receptacle, a restraining cup being mounted in said open outer end of said receptacle, said restraining cup having a closed outer end and an open inner end, said pouch being retained in place by engagement with said open inner end of said restraining cup and said partially closed inner end of said receptacle, said restraining cup further containing an unrestrained member disposed between said outer end of said restraining cup and said pouch, said unrestrained member being arranged to move reciprocally within said restraining cup when said capsule is vibrated in a vibrating mixer so as to impact against said pouch and rupture said pouch at said partially closed inner end of said receptacle for enabling said liquid component to admix with said powder component to form a dental paste simultaneously with vibration, wherein said compartment of said hollow body adjacent said first end is provided with a manually removable cap, said first and second ends of said hollow body being separated by an internal circumferential flange, and said receptacle is mounted in said second end of said hollow body such that said partially closed inner end is engaged with said internal circumferential flange, so as to define said compartment in said hollow body adjacent said first end thereof containing said dental powder component.

2. A dental capsule according to claim 1, wherein said pouch comprises a pair of opposed layers defining a volume.

3. A dental capsule according to claim 2, wherein said pouch has edges which are sealed together and said edges are sandwiched between said inner end of said restraining cup together with said inner end of said receptacle.

4. A dental capsule according to claim 1, wherein said inner end of said receptacle is provided with a relatively small central aperture.

* * * * *